United States Patent [19]
Welsh

[11] Patent Number: 6,102,449
[45] Date of Patent: Aug. 15, 2000

[54] CONNECTOR FOR CAPILLARY TUBING

[75] Inventor: Paul B. Welsh, Wilmington, Del.

[73] Assignee: Agilent Technologies, In., Santa Clara, Calif.

[21] Appl. No.: 09/182,044

[22] Filed: Oct. 29, 1998

[51] Int. Cl.[7] .................................................. F16L 19/00
[52] U.S. Cl. ......................... 285/342; 285/343; 285/332; 285/351; 285/375
[58] Field of Search ................................. 285/343, 342, 285/332.2, 332.3, 351, 375, 19, 20, 332

[56] References Cited

U.S. PATENT DOCUMENTS

| | | | |
|---|---|---|---|
| 1,871,370 | 8/1932 | Jacques | 285/375 |
| 3,341,231 | 9/1967 | Johanson | 285/342 |
| 3,996,017 | 12/1976 | Kaiser . | |
| 4,281,679 | 8/1981 | Stearns | 285/342 |
| 4,451,365 | 5/1984 | Sattler et al. . | |
| 4,474,889 | 10/1984 | Terry et al. . | |
| 4,669,756 | 6/1987 | Cassaday et al. . | |
| 4,679,824 | 7/1987 | Rodriquez et al. | 285/332 |
| 4,758,340 | 7/1988 | Marchand et al. . | |
| 4,776,618 | 10/1988 | Barree . | |
| 4,787,656 | 11/1988 | Ryder . | |
| 4,969,938 | 11/1990 | America . | |
| 4,991,883 | 2/1991 | Worden . | |
| 5,105,652 | 4/1992 | Manfredi et al. . | |
| 5,163,215 | 11/1992 | Ledford . | |
| 5,163,722 | 11/1992 | Worden . | |
| 5,215,340 | 6/1993 | Ledford . | |
| 5,234,235 | 8/1993 | Worden . | |
| 5,236,668 | 8/1993 | Higdon . | |
| 5,288,113 | 2/1994 | Silvis et al. . | |
| 5,298,225 | 3/1994 | Higdon . | |
| 5,540,464 | 7/1996 | Picha . | |
| 5,544,276 | 8/1996 | Loux et al. . | |
| 5,559,283 | 9/1996 | Kaji et al. . | |
| 5,578,157 | 11/1996 | Higdon . | |
| 5,601,785 | 2/1997 | Higdon . | |

FOREIGN PATENT DOCUMENTS

| | | |
|---|---|---|
| 0545843 | 6/1993 | European Pat. Off. . |
| 2202578 | 7/1973 | Germany ............................. 285/351 |
| WO92/04958 | 4/1992 | WIPO . |

OTHER PUBLICATIONS

A. Spark, "Simple, Universal Joining System For Glass to Silica Capillary Tubing;" Journal of High Resolution Chromatography & Chromatography Communications; Aug. 1986, pp. 481–482.

E.R. Rohwer, V. Petorius, & P.J. Apps, "Simple Press–Fit Connectors for Flexible Fused Silica Tubing in Gas–Liquid Chromatography;" Journal of High Resolution Chromatography & Chromatography Communications, May, 1986, pp. 295–297.

(List continued on next page.)

*Primary Examiner*—Lynne H. Browne
*Assistant Examiner*—Aaron Dunwoody

[57] ABSTRACT

Fluid connector for connecting a first fluid-bearing conduit in a capillary tube to a second fluid-bearing conduit in a receiver. An internal fitting assembly includes an internal fitting body, a body cavity for receiving a ferrule and a self-compensating nut, the ferrule and self-compensating nut being locatable on the capillary tube, and an internal ferrule seat located on a portion of the body cavity, against which a tapered portion of the ferrule is applied to so as to obtain a first fluid-tight seal between the capillary tube, the ferrule, and the ferrule seat. The forward end of the internal fitting body includes a nose cone, having thereon an annular projection, a neck portion which connects the nose cone to the remainder of the internal fitting body, and an annular seal located on the neck portion, wherein the annular projection defines a first frustoconical segment and the annular seal includes a second frustoconical segment, the first and second frustoconical segments being configured to establish a second fluid-tight seal at the receiver port surface as the forward end of the internal fitting body is coaxially aligned with the receiver port and thrust into the receiver cavity.

8 Claims, 3 Drawing Sheets

OTHER PUBLICATIONS

K. Grob, "Elastic Fittings for Glass Capillary Columns;" Journal of High Resolution Chromatography & Chromatography Communications, Aug., 1978, pp. 103–104.

Konad Grob, Maurus Biedermann, Konrad Bernath, & Hans–Peter Neukom; "Call for Fused Silica Tubing Furnishing Tight Press–Fit Connections;" Journal of High Resolution chromstography, Sep., 1992, pp. 613–614.

Clas Wesen & Huiling Mu; "Re–Use of Press–Fig Connectors and Splitters for GC Capillary Columns" Journal of High Resoultion Chromatography, p. 136.

Konrad Grob & Hans–Peter Neukom, "Ruined GC Column Performance due to Ferrule Particle;" Journal of High Resolution Chromatography, Vol 13, Sep. 1990, pp. 658–659.

CONNECTOR FOR CAPILLARY TUBING

FIELD OF THE INVENTION

The present invention relates to apparatus for coupling a fluid stream in a first fluid-bearing conduit to a second fluid-bearing conduit.

BACKGROUND OF THE INVENTION

Connectors are known in the art for receiving a fluid stream in a first fluid-bearing conduit and then delivering the received fluid stream to a second fluid-bearing conduit. In many cases, the fluid connection is obtained by manual alignment and coupling of separate components that comprise the connector, such as by alignment and compression of a sealing device onto a tubular device while being fitted to a receiving fitting.

The sealing device on conventional connectors is typically a ferrule having a conical frustrum exterior and a through hole. The tubular device is inserted into the through hole and the tubular device/ferrule assembly is then inserted into a receiving feature which is shaped as a complementary conical frustrum. The receiving feature is referred to as the ferrule seat. The tubular device/ferrule assembly is then forced into the ferrule seat via pressure applied by a threaded fastener.

Such an approach has several disadvantages. To effect a reliable, fluid-tight seal, the leading edge of the exterior of the ferrule must be properly oriented to the ferrule seat, which occurs only if the central axes of the ferrule and ferrule seat are perfectly coincident; both the ferrule and the ferrule seat must be fabricated to be perfectly circular; the diameter of the through hole in the ferrule must be uniformly and adequately compressed to effect a seal between the surface of the through hole and the exterior surface of the column; and the exterior of the ferrule must be uniformly and adequately compressed to effect a seal between the ferrule and the interior surface of the receiver fitting.

Other problems arise when the connector and the tubular device are subject to extended periods in a variable temperature environment. For example, in gas chromatography, a connector may be employed on a tubular device in the form of a capillary column to couple a fluid stream in the column to certain devices (such as a detector) in a chromatographic apparatus. The column may be located in a convection oven wherein the temperature environment ranges from minus 70 degrees C. to 450 degrees C. Conventional connectors, when used in such an environment, are subject to expansion and contraction. Fittings within a connector are subject to cyclical deformation, resulting in cracks. As a result, the connection fails and the connector is subject to leakage. The results of such a failure include: degradation of the column via oxidation; poor quantitation due to inaccurate measurement of column flow; interference effects of air at the detector; and degradation of analytes in the fluid stream as they react with the atmosphere.

Furthermore, most connectors are difficult to install correctly, especially by operators with minimal skills and training. Even connectors that appear to be properly installed can develop a leak at installation, which is very difficult to detect; however, the subsequent analytical run will suffer from column degradation (from oxygen diffusion), and quantitation errors. The pilot depth (i.e., the depth of the exposed tip of the column in an associated receiving device such as an inlet or a detector) is important for proper operation. The operator must measure the pilot depth when the column is installed, but this measurement is difficult and subject to error. Good laboratory practice also dictates that, upon replacement or reinstallation of a column, the ferrule should be replaced. Replacement is often a difficult or tedious procedure. For example, certain components in the connector may have become seized and are difficult or impossible to remove. Furthermore, during installation of a new connector, the column tip must be threaded through a small hole in the new ferrule, and dust or particles from the new ferrule often contaminate the column tip.

One conventional approach to resolving some of the foregoing difficulties includes a practice of fabricating the ferrule from a compliant material, such as graphite. A large insertion force is then used to force the ferrule into the ferrule seat, thus causing the ferrule to conform both to the shape of the ferrule seat and to the exterior of the capillary tube. The drawback to this approach is that a high stress is induced in the ferrule by such compression. Further, a high temperature environment will often cause such ferrule material to creep or fracture, thereby creating a fluid leak.

Another approach is to use ferrules and ferrule seats that each have a small included angle; however, a problem arises in that such a ferrule/seat combination is still prone to fracture or seizure (jamming) of the ferrule in the ferrule seat. Neither the ferrule nor the ferrule/seat combination is easily replaced.

Thus, a routine column removal, replacement, or installation task becomes an expensive and time-consuming process.

Still another approach is to encapsulate the ferrule material in a rigid container to comprise a ferrule assembly; however, such a ferrule assembly, when subjected to extremes in temperature, appears to suffer from thermally-induced mechanical creep, which can cause a leak.

Another approach is to utilize a spring-loaded ferrule (see, e.g., U.S. Pat. No. 5,163,215) so as to compensate for thermally-induced mechanical creep. This approach has the potential to prevent failures that are due to creep-induced leaks. However, the conventional spring-loaded ferrule requires a high spring force to achieve an adequate seal, which necessitates the use of a large spring and various other parts to provide a spring assembly. The ferrule/seat combination is also prone to fracture or seizure of the ferrule in the ferrule seat.

There remains a practical need for a simple, reliable, and inexpensive connector for receiving a fluid stream in a first fluid-bearing conduit and delivering the fluid stream into a second fluid-bearing conduit without incurring leaks or other failures. This need is especially apparent in environments that require fast and easy installation of a capillary column to an analytical instrument without resort to the use of tools or specialized installation techniques. Further, there is a need for a simple, reliable, and inexpensive connector that facilitates removal, replacement, or re-installation of such a capillary column.

SUMMARY OF THE INVENTION

The contemplated fluid connector constructed according to the present invention is advantageously employed for easily and reversibly connecting a first fluid-bearing conduit situated in, e.g., capillary tube, in fluid-tight communication with a second fluid-bearing conduit situated in a receiving portion of the connector (termed hereinafter as a receiver). The fluid connector provides an improved means for connecting the first fluid-bearing conduit to the second fluid-bearing conduit for leak-free operation in a high temperature environment. Disassembly of the first fluid-bearing conduit from the receiver may be performed easily and without damage to the first or second fluid-bearing conduits, and without other failure modes that otherwise would occur due to the effects of the connection or the temperature environment.

Accordingly, the present invention provides a novel fluid connector for connecting a first fluid-bearing conduit to a second fluid-bearing conduit, thereby providing a reliable and substantially leak-free fluid seal between the first and second fluid-bearing conduits. (For the purposes of this description, "fluid-bearing" refers to a characteristic of a device that denotes its' capability for conveying a fluid stream at some time in the operation of the device.)

The first fluid-bearing conduit is preferably located in an open tubular device provided in the form of an open-ended capillary tube. The second fluid-bearing conduit is preferably located in the receiver and communicates with a receiving port that is integrated within the receiver. The receiver also includes a receiver port surface, which preferably is frustoconical, which in turn defines a receiver cavity.

A preferred embodiment of a connector for coupling the capillary tube to the receiver accordingly includes an internal fitting assembly having an internal fitting body, wherein there is a body cavity within which there may be mounted a ferrule and a self-compensating nut. The ferrule and the self-compensating nut may be pre-fitted with the ferrule to the capillary tube. A portion of the body cavity is defined by an internal ferrule seat, against which a tapered portion of the ferrule may be applied; the fluid-tight seal between the ferrule and the ferrule seat is maintained due to the pressure of a compensating spring in the self compensating nut. The ferrule is provided with a central bore, an aft end having aft transverse surface that is perpendicular to the central axis of the bore, and a forward end having a frustoconical tapered portion, wherein the central bore extends therebetween for receiving the capillary tube and for aligning the ferrule with respect to the exterior surface of the tube. The central bore is sized and shaped for a snug but nonetheless slidable fit to the exterior of the capillary tube.

The internal fitting assembly is preferably pre-assembled on the capillary tube, whereby the ferrule engages a fluid seal on the exterior of the tube. The capillary tube, with the internal fitting assembly mounted thereon, may be inserted into a body cavity in the internal fitting body until the tip of the capillary tube extends through a central bore in the forward end of the internal fitting body. As the compensating nut is threaded into the body cavity of the internal fitting body, the ferrule is urged, by action of the compensating nut, onto a corresponding portion of the body cavity that defines a ferrule seat. The capillary tube is subjected to radial compression so as to attain complete and intimate seal between the exterior of the capillary tube and the ferrule, and the forward surface of the ferrule is subject to radial compression against the ferrule seat, so as to attain a complete and intimate seal between the capillary tube, the ferrule, and the ferrule seat.

The forward end of the internal fitting body includes a nose cone, having thereon an annular projection, and a neck portion which connects the nose cone to the remainder of the internal fitting body. An annular seal may be mounted on the neck portion at a position immediately posterior to the nose cone. The annular projection preferably defines a first frustoconical segment, and the annular seal includes a second frustoconical segment. Upon mounting the annular seal to the neck, the first and second frustoconical segments are configured to complement a corresponding frustoconical portion of the receiver port surface and thus are configured to contact the receiver port surface as the forward end of the internal fitting body is coaxially aligned with the receiver port and thrust into the receiver cavity.

The annular seal is preferably composed of deformable material such that the second frustoconical segment conforms to, and obtains a fluid-tight seal with, a corresponding portion of the receiver port surface. Most preferably, the annular seal includes a central bore, is generally shaped as an O-ring but with the second frustoconical surface segment, and is formed of a resilient material such that it is reusable. This most preferably preferred embodiment of the annular seal may be removably fitted over the nose cone and onto the neck portion for easily installation or removal. When installed, the annular seal is snugly fitted against an aft side of the annular projection such that there is little or no discontinuity between the first and second frustoconical segments.

When the forward end of the internal fitting body engages the receiver, the first and second frustoconical segments are simultaneously impressed upon the receiver port surface. Accordingly, the internal fitting body includes biasing system, including a biasing spring for providing a biasing force and a compression collar for coupling the biasing force to the aft transverse surface of the annular seal in a direction parallel to the central axis of the internal fitting body, and for uniformly distributing the biasing force to the aft transverse surface of the annular seal. The biasing system thus exerts a predetermined biasing force so as to: a) urge the annular seal against the aft side of the annular projection of the nose cone, so as to reduce or eliminate any discontinuity between the first and second frustoconical segments; b) urge both the first and second frustoconical segments against corresponding first and second portions of the receiver port surface, so as to reduce or eliminate the dead volume in the receiver cavity; c) simultaneously urge the annular seal against the aft surface of the annular projection, and urge the second frustoconical segment (which is on the annular seal) to conform to the receiver port surface, so as to form a fluid-tight seal between the forward end of the internal fitting body and the receiver port surface.

In a particular feature of the invention, the receiver and the internal fitting assembly are provided as separable components such that the receiver may be mounted on a first support and the internal fitting assembly may be mounted on a second support, such that the internal fitting assembly may be quickly and easily engaged in the receiver by juxtaposition of the first and second supports.

In another particular feature of the invention, the receiver and the internal fitting assembly are provided as separable components such that the forward end of the internal fitting assembly is easily inserted into the receiver cavity by hand or by automated positioning techniques. Hence, because the internal fitting assembly may be pre-assembled on the capillary tube, whereupon a first seal is obtained between the ferrule and the capillary tube, and by the provision of a second seal obtained between the annular seal and the receiver port surface when the internal fitting assembly engages the receiver, a fluid-tight seal may be realized without resort to specialize techniques or tools. Furthermore, several additional advantages are realized:

Firstly, the requisite radial compression force applied to the ferrule is greatly reduced in comparison to the biasing force necessary for effecting a seal in the connectors disclosed in the prior art. Secondly, the amount of dead volume present between the forward end of the internal fitting assembly and the receiver cavity is decreased, while lowering the biasing force required for effecting an adequate seal of the in your seal to the receiver port surface. Thirdly, the nose cone minimizes or prevents the transit of potentially damaging fluid from the tip of the capillary tube to the annular seal. Fourth, the engagement of the internal fitting assembly into the receiver is self-directing, i.e., the first frustoconical segment tends to be coaxially aligned with, and into, the receiver port surface, such that the requisite seal between the internal fitting assembly and the receiver is easily and quickly obtained by an operator without resort to the use of tools or specialized techniques for obtaining the desired fluid-tight connection.

The annular seal is biased by a biasing system so as to realize a fluid-tight seal between the receiver port surface and the aft portion of the annular projection. Because the connector employees the above described two-part assembly, the annular seal need not contact with the capillary tube, and accordingly it has no opportunity to adhere to the exterior of the capillary tube (in contrast to conventional apparatus wherein a ferrule or similar device is subject to seizure on the polyimide surface of a capillary column).

Also, the aft surface of the annular projection is configured to retain the annular seal when the forward end of the internal fitting assembly is withdrawn from the receiver (during, e.g., a procedure in which the capillary tube must be removed, replaced, or examined.) Accordingly, in an instance of adhesion of the annular seal to the receiver port surface, the annular seal is nonetheless easily withdrawn.

The annular seal is preferably made of a deformable material so as to accommodate slight misalignment in the orientation of the nose cone with respect to the receiver port surface, and to accommodate most variations in the dimensions of the receiver and of the annular seal itself, thus ensuring a reliable, fluid-tight seal without resort to tedious alignment or assembly procedures, specialized tools or fasteners, or a high compression force. In particular, a predetermined amount of compression force on the annular seal is provided by the biasing system not only to ensure that it is sufficient for sealing purposes, but also to allow for the seal to be accomplished manually, i.e., without resort to the use of threaded fasteners, and the like. The deformable characteristic of the annular seal also accommodates dimensional changes of the various parts in the Internal fitting assembly caused by cyclical temperature variations.

In another aspect of the invention, because the central bore in the annular seal may be constructed to be relatively large compared to the diameter of the tip of the capillary tube, and because the forward end of the capillary tube is securely located by the central bore of the nose cone, the annular seal can be easily installed or removed over the tip of the column without causing contamination of the capillary tube.

In another aspect of the invention, both the annular seal and the ferrule are spring-loaded to maintain pressure on any respective contiguous surfaces and thereby creep or other deformation it is circumvented.

In another aspect of the invention, the seal obtained between the ferrule and the capillary tube need only be made once, such that the self-compensating nut and the ferrule may remain attached to the capillary tube as it is installed, removed, or re-installed in a receiver. Furthermore, because the capillary tube is pre-fitted to the internal fitting assembly, the pilot depth may be preset and does not vary during repeated removal or re-installation of the capillary tube in the connector. This advantageous step of pre-fitting of the capillary tube to the internal fitting assembly may be accomplished during manufacturing, or by an operator during installation of the capillary tube in an analytical instrument.

Accordingly, a preferred embodiment of the system is provided in the form of a connector preferably suited for connecting an open capillary column to a receiver integrated in a sample analysis system. The connector thus employed will enable analysis of the constituent components of a sample fluid carried in the capillary column and provided to or from the capillary column by a receiver. The receiver may be integrated in an inlet, a detector, or other fluid-handling functional device.

DETAILED DESCRIPTION OF THE INVENTION

The present invention will find useful application in a variety of fluid handling systems that benefit from the delivery or connection of a discrete or continuous flow of a fluid stream. Such fluid handling systems are especially employed in a wide variety of analytical applications, such as sample extraction, purification, and analysis; clinical assay and analysis; industrial processing; and reagent dispensing. Further examples of instruments that are particularly benefited by an application of the present invention include instruments for performing gas, liquid, or supercritical fluid chromatography. In particular, the preferred embodiment is especially suited for connecting capillary tubing to a fluid receiver integrated in a fluid handling functional device present in a gas or liquid chromatograph.

Figure 1:
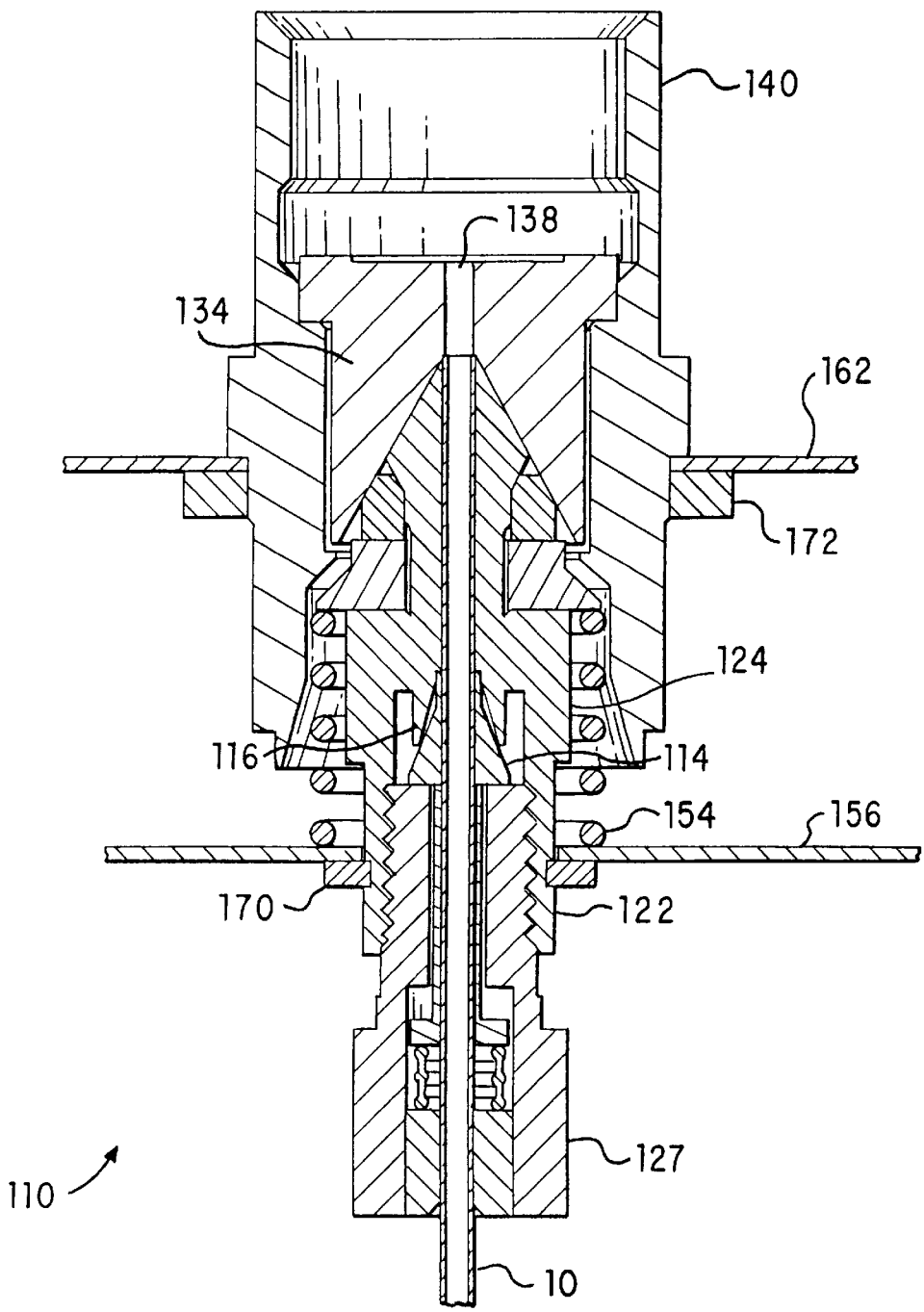
FIG. 1 is a side sectional view of the connector of the present invention.
Figure 2:
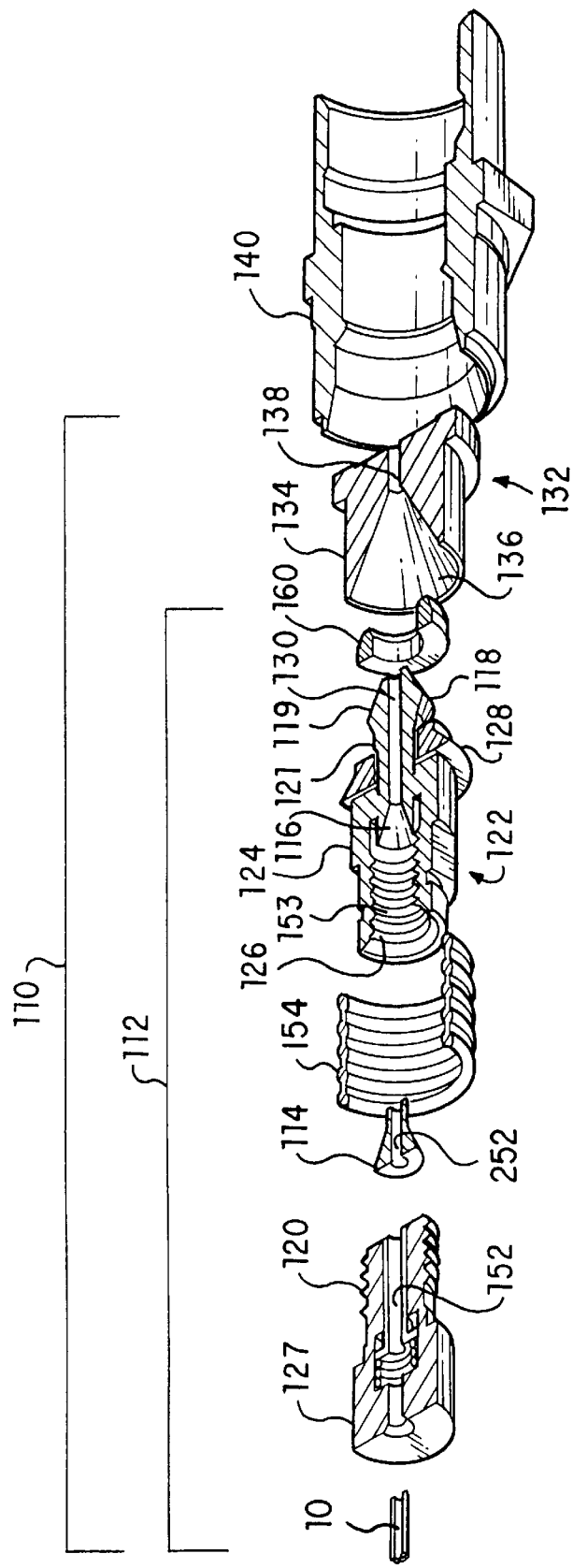
FIGS. 2 and 3 are a side sectional and perspective views, respectively, of the connector of FIG. 1, in an exploded arrangement for clarity.
Figure 3:
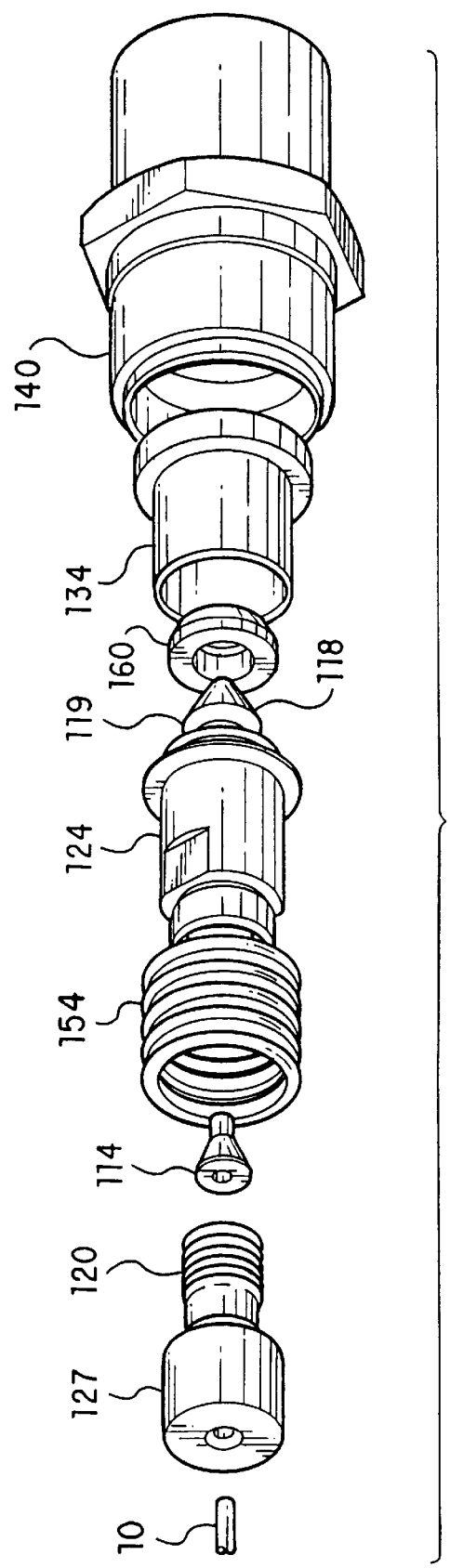

Accordingly, FIGS. 1–3 illustrate a preferred embodiment of a fluid connector constructed in the form of a connector assembly 110. The illustrated fluid connector is especially suited for connecting a fluid stream within a sample analysis system operable for accomplishing a chromatographic separation and detection of various components in a sample present in the fluid stream.

The illustrated connector assembly 110 includes an internal fitting assembly 112 contemplated for use in connecting a first fluid-bearing conduit in the form of an open tubular or open capillary silica column 10 (also referred to herein as a capillary tube, a capillary column, or simply a tube, or a column) to a receiver 132 that may include, or is integral with, a second fluid-bearing conduit in the form of a channel 138. Receiver 132 includes a receiver port body 134 having a receiver port surface 136. The central bore 138 communicates between a forward end of receiver port surface 136 and a housing 140. The receiver port body 134 may be suitably engaged or integrated in the housing 140 which is mounted on a housing support 162 by suitable means such as a retainer 172. The configuration and structure of the housing 140 may vary according to the particular application of the connector 110. For example, the housing 140 may be configured as a portion of an inlet, detector, or other fluid handling functional device and the support 162 may be configured as a portion of chamber or compartment wall in an analytical instrument.

The internal fitting assembly 112 includes a body 122 that has a generally cylindrical wall 124 provided with internal grooves 126 which mate with threads 120 on a forward end of a self compensating nut 127, so as to allow the self compensating nut 127 to engage the body 122. The body 122 further includes a shoulder flange 128 that is preferably coaxially slidable along a neck 121. The body 122 has a generally centrally disposed, cylindrical bore 130 extending between a ferrule seat 116 and a nose cone 118 which is located at the forward end of the body 122. A compression spring 154 is mounted between the shoulder flange 128 and the support 156. Accordingly, the spring 154 will act to urge shoulder flange 128 away from support 156 when be internal fitting assembly 112 is attached to support 156. As a result, when support 156 is positioned proximate to and parallel with support 162, the spring 154 causes the forward end of the internal fitting assembly 112 to engage the receiver 132, as will be described in greater detail below.

Particular features of the nose cone 118 include an annular projection 119 that extends radially from the junction of the nose cone 118 and neck 121. A annular seal 160 is fitted over the annular projection 119 and onto the neck 121; the shoulder flange 128 is movable along neck 121 so as to transfer a compression force provided by spring 154 to the aft end of annular seal 160.

The body 122 also defines a generally cylindrical cavity 153 in which the forward end of the self compensating nut 127 and a ferrule 114 are received upon assembly. The tip of a capillary tube 10 is threaded through a central bore 152 in the self compensating nut 127 and through central bore 252 in the ferrule 114 and through central bore 130 in body 122 so as to be extending therefrom (i.e. at a pilot depth extending from the nose cone).

The connector 110 thus provides a means to provide fluid-tight communication between a capillary tube and a fluid-bearing conduit in a receiver, i.e., between the capillary tube 10 and the channel 138. The fluid-tight seal is maintained even when subject to temperature extremes because the biasing action of the spring 154 will maintain the annular seal 160 in contact with the receiver 132.

While the biasing system is shown as a spring 154, it will be recognized that another system of biasing the body 122 can be employed, such as one or more flexural members; helical coils; corrugated leaves; resilient cylinders, pads, or toroids; etc. Use of a spring 154 formed of quartz or similar material has particular advantage when the connector is to be used in very high temperature environments where metallic springs might yield or fail.

In a particularly advantageous aspect of the invention, the preferred embodiment of a fluid connector 110 features a separable, two-part design, wherein the major components of which are considered herein as the receiver 132 and the internal fitting assembly 112, and wherein the internal fitting assembly 112 includes at least two distinct, fluid-tight seal functions: a first seal is provided by a combination of the self compensating nut 127 and a ferrule 114 for effecting a fluid-tight seal between the capillary tube 10 and the internal fitting assembly 112, and a second seal is provided between the forward end of the body 122 and the receiver port surface 136 in the receiver 132. In particular, the receiver port surface 136 of the receiver 132 is provided with a frustoconical egress that complements a combination of a first complementary frustoconical segment of the nose cone 119 and a second complementary frustoconical segment on the annular seal 160.

The foregoing components of the internal fitting assembly 112 are simple and inexpensive to construct and therefore it is contemplated that the internal fitting assembly may be pre-mounted on the capillary tube 10 during manufacturing of the capillary tube 10, whereupon the combined internal fitting assembly and capillary tube may be provided as one unit. Furthermore, the annular seal 160 is inexpensive, replaceable, and disposable or recyclable.

The second fluid-tight seal feature is easily established by manual insertion of the internal fitting assembly 112 into the receiver 132. That is, the configuration of the nose cone 119 allows forward end of the internal fitting assembly 112 to be easily aligned with, and loaded against, the frustoconical receiving surface 136 in the receiver 132. The frustoconical receiving surface 136 offers a conical egress having a large included angle. Accordingly, a small, low-force biasing spring 154 may be used to maintain sealing contact of the first and second frustoconical segments to the receiver port surface 136 in the receiver 132. A reliable fluid seal is maintained at a low spring force and without further adjustment or tightening of the ferrule 114 or self compensating nut 127. The spring 154 therefore exhibits less thermal mass than the devices used for effecting a sealing function in the prior art. The self compensating nut 127 is similar to one commercially available from Valco instruments Company, Houston, Texas as product number FSZNA-HP.

Also, the provision of the second seal (between the annular seal 160 and the receiver port surface 136) obviates the necessity, often seen in the prior art, for machining parts to extremely close tolerances in an attempt to achieve mated, gas-tight engagement between relatively large contact surfaces.

The components of the connector 110 can be fabricated from a variety of materials. The annular seal 160 is preferably made of a deformable material that exhibits at least some capacity for deformation at a minimum (and hence is considered to be deformable) or, more preferably, is made of a resilient material that exhibits not only some capacity for deformation and some additional characteristic of elasticity. Accordingly, the term "deformable" as used herein refers to a material which, under compression, deforms to the extent necessary to achieve a fluid-tight seal between the neck 121 and the corresponding contiguous portion of the receiver port surface 136. The term "resilient" as used herein refers to a material which, under compression, deforms to the extent necessary to achieve engagement between the neck 121 and the corresponding portion of the receiver port surface 136 and also is capable of resuming a sufficient amount of its original shape when such engagement is undone, such that the annular seal 160 is reusable. Suitable resilient materials include: silicone rubber; perfluoroelastomers, such as those available from the DuPont Company (Wilmington, Del.) under the trade name "Kalrez"; fluoroelastomers, such as those available from the DuPont Company (Wilmington, Del.) under the trade name "Viton"; or various other polymeric mixtures which are resilient as that term is used above. Suitable deformable materials include: graphite; inert polymers or polyimides, aramid polymers, acetal resins, and poly (tetrafluoroethylene) such as those available from the DuPont Company (Wilmington, Del.) under the trade names "Vespel", "Kevlar", "Delrin", and "Teflon", respectively; and poly(chlorotrifluoroethylene), such as those available from the 3M Company (Newark, N.J.) under the trade name "Kel-F". Deformable materials are also preferred for use in providing the ferrule 114.

It is also preferred that the majority of the remaining components of the connector 110 be formed of metal, such as stainless-steel, although inexpensive (thus disposable), inert, thermally-stable materials may be chosen for certain components, such as an organic polymer; or an inert polymers such as polyimides, aramid polymers, acetal resins, and poly(tetrafluoroethylene) and poly (chlorotrifluoroethylene), The means for attachment of the integral fitting assembly 112 to the support 156 may include a snap ring 170 as shown; the housing 140 may be retained on support 162 by similar means such is a retainer 172. The foregoing attachment or retaining devices may be replaced or augmented with a differing type of retention device, or by a threaded, socketed, or friction-fitting retaining device(s) of differing construction known in the art. in most applications, the attachment of the internal fitting assembly 112 to the receiver 132 is intended to be reversible or releasable so as to allow the internal fitting assembly 112 to be removed from the support 156 and disassembled for servicing or replacement of the internal fitting assembly 112 or the capillary tube 10.

The fluid connector 110 is expected to maintain a reliable fluid-tight seal even after experiencing wide variations in the temperature environment and during conditions of low compression (sealing) force, angular misalignment, and/or variations in the included angle of the receiver port surface 136.

The broad included angle on the frustoconical receiver port surface 136 allows an adequate seal to be made between the forward and of the internal fitting 112 with use of less insertion force than the assembly or sealing forces encountered in prior art fluid connectors. Assembly and disassembly of the connector is thus reliable and easy. Nonetheless, should the ferrule 114 become jammed into body 122 (i.e., nearly or completely inseparable), they may be easily removed from the connector 110 even while the column 10 is still attached. The column 10 may then be cut at a point adjacent the ferrule 114, and the tube fragment and ferrule 114 are then discarded. A new ferrule 114 may then be easily and inexpensively employed to re-establish a fluid-tight connection.

The advantages of the foregoing capabilities for servicing or replacement of the connector 110 will distinguish it as a low-cost, effective device for effecting fluid-tight connections. As described in the foregoing, the connector 110 of the present invention is preferred for the delivery of fluid stream in a capillary column 10 to one or more channels 136 in a fluid handling functional device in a sample analysis system. However, the contemplated connector 110 will find application for the delivery of a fluid stream to or from differing or additional components that may be present in the sample analysis system, or in other fluid handling systems. For example, the contemplated fluid connection for delivery of a fluid stream is not limited to only a capillary tube 10. It will be appreciated that the connector 110 may be fitted to other components such as tubular fittings, piping, tube, needles, canulas, drains, nipples, and other apparatus or devices. While such systems are not shown in the figures, they are contemplated as being amenable to use with the present invention.

Although the invention has been described with reference to the above-described preferred embodiments, variations and modifications are contemplated as being within the scope and spirit of the present invention.

What is claimed is:

1. A connector for connecting a first fluid-bearing conduit to a second fluid-bearing conduit, thereby providing fluid communication between the first and second fluid-bearing conduits, the first fluid bearing conduit being located in a capillary tube and the second fluid-bearing conduit being located in a receiver and communicating with a receiver port having a receiver port surface, comprising:

an internal fitting assembly having an internal fitting body, a body cavity for receiving a ferrule and a self-compensating nut, said ferrule and self-compensating nut being locatable on the capillary tube, and an internal ferrule seat located on a portion of the body cavity, against which a tapered portion of the ferrule is applied to so as to obtain a first seal between the capillary tube, the ferrule, and the ferrule seat;

wherein a forward end of the internal fitting body includes a nose cone, having thereon an annular projection, a neck portion which connects the nose cone to the remainder of the internal fitting body, an annular seal located on the neck portion, wherein the annular projection defines a first frustoconical segment and the annular seal includes a second frustoconical segment, the first and second frustoconical segments being configured to contact the receiver port surface as the forward end of the internal fitting body is coaxially aligned with the receiver port and thrust into the receiver cavity, and a biasing system for coupling a biasing force to an aft transverse surface of the annular seal in a direction parallel to the central axis of the internal fitting body, so as to: a) urge the annular seal against an aft surface of the annular projection of the nose cone, so as to reduce discontinuity between the first and second frustoconical segments; b) urge both the first and second frustoconical segments against corresponding first and second portions of the receiver port surface, so as to reduce dead volume in the receiver cavity; c) simultaneously urge the annular seal against the aft surface of the annular projection and urge the second frustoconical segment to conform to the receiver port surface, so as to form a second fluid-tight seal between the forward end of the internal fitting body and the receiver port surface.

2. The connector of claim 1, wherein the biasing system further comprises a biasing spring and a compression collar located on the neck portion and movable thereon, wherein the biasing spring is located for providing a biasing force to the compression collar and a compression collar it is located for coupling the biasing force to the annular seal.

3. The connector of claim 1, wherein the annular seal further comprises a deformable material.

4. The connector of claim 1, wherein the annular seal further comprises a central bore and is generally shaped as an O-ring having thereon the second frustoconical surface segment.

5. The connector of claim 1, wherein the annular seal further comprises a resilient material such that it is reusable.

6. The connector of claim 1, wherein the receiver and the internal fitting assembly are provided as separable components such that the receiver may be mounted on a first support and the internal fitting assembly may be mounted on a second support, whereby the internal fitting assembly may be quickly and easily engaged in the receiver by juxtaposition of the first and second supports.

7. The connector of claim 1, wherein the internal fitting assembly is pre-assembled on the capillary tube, whereupon the first seal is obtained between the ferrule and the capillary tube.

8. The connector of claim 1, wherein the aft surface is configured to retain the annular seal when the forward end of the internal fitting assembly is withdrawn from the receiver.

* * * * *